United States Patent [19]
Allen, Jr.

[11] 4,267,620
[45] May 19, 1981

[54] METHOD AND APPARATUS FOR CONTROLLING TEXTILE WORKING SYSTEMS EMPLOYING NMR DETECTOR

[75] Inventor: John D. Allen, Jr., Knoxville, Tenn.

[73] Assignee: Special Instruments Laboratory, Inc., Knoxville, Tenn.

[21] Appl. No.: 934,536

[22] Filed: Aug. 17, 1978

[51] Int. Cl.³ .................. G01R 33/08; D01H 5/32
[52] U.S. Cl. ........................ 19/239; 324/300
[58] Field of Search .......... 324/0.5 R, 300, 306, 324/307; 19/239, 240

[56] References Cited

U.S. PATENT DOCUMENTS

| | | | |
|---|---|---|---|
| 2,891,287 | 6/1959 | Raper | 19/239 |
| 2,981,986 | 5/1961 | Neil | 19/240 |
| 3,021,475 | 2/1962 | Cennamo | 324/0.5 R |
| 3,305,688 | 2/1967 | Lamparter | 19/239 X |
| 3,419,793 | 12/1968 | Genthe et al. | 324/306 |
| 3,441,984 | 5/1969 | Bryan et al. | 19/239 X |
| 3,471,774 | 10/1969 | Muschinske et al. | 324/306 |
| 3,529,234 | 9/1970 | Keen | 324/300 |
| 4,110,680 | 8/1978 | Bergmann et al. | 324/306 |

FOREIGN PATENT DOCUMENTS 212094  2/1957  Australia ............... 19/239

*Primary Examiner*—Gerard R. Strecker
*Attorney, Agent, or Firm*—Burns, Doane, Swecker & Mathis

[57] ABSTRACT

The present disclosure relates to a method and apparatus for controlling textile working systems such as drafting frames. A detector is provided for detecting variations in the numbers of specific types of atoms, such as hydrogen atoms, in a known length of a traveling fibrous strand being worked by the drafting frame or other textile working device. System parameters, such as the draft imparted to the strand, may be varied in response to the detected variations.

10 Claims, 2 Drawing Figures

METHOD AND APPARATUS FOR CONTROLLING TEXTILE WORKING SYSTEMS EMPLOYING NMR DETECTOR

BACKGROUND OF THE DISCLOSURE

The invention relates to a method and apparatus for controlling textile working systems responsive to the numbers of certain types of atoms, such as hydrogen atoms, detected in a length of an elongated fibrous strand being worked. Thus, the present invention relates to a method and apparatus useful for controlling drafting systems by sensing the traveling textile material. Prior art patents, relating generally to such a method and apparatus, are believed to be classified by the U.S. Patent Office in class 19, subclass 239.

In the manufacture of yarn and other elongated fibrous strands, it is desirable to achieve a degree of uniformity in the product throughout the length of the product so that both short range irregularities and long range drift in the product are reduced or eliminated. As a first step toward this goal, short term irregularities and long term drift in the product must be satisfactorily detected. Data concerning the uniformity of the product may then be employed to control the textile working system.

In known textile working systems, control of the product uniformity has been attempted at the drafting frame, where slivers are attenuated to promote parallelization. Of course, some rudimentary control can be achieved by periodically removing samples of the slivers, measuring and weighing the samples, calculating an average mass per unit length of the sliver, and adjusting the draft ratio of the drafting frame or other system parameter in accordance with the calculated average of the sample. Obviously, this approach provides control data only after the delay engendered by the testing process. Unless the sampled silver is of sufficient length and is reintroduced into the production line, this procedure constitutes destructive testing. Moreover, local variations in the sliver are not detected since an average mass per unit length is calculated. Thus, the procedure cannot be used for continuous control of the drafting frame or to detect periodic short term variations in the slivers, the period of which is indicative of a particular malfunction in the textile working system.

Accordingly, it is an object of the present invention to provide a method and apparatus for continuously and accurately controlling a textile working system by sensing the traveling fibrous output product of the system.

It is another object of the present invention to provide a method and apparatus for controlling a textile working system responsive to both short term and long term variations in the product.

Over the past twenty years, a large number of detector devices have been proposed for continuously sensing a traveling textile product: measurement of the photon absorption of the strand (see U.S. Pat. No. 3,305,688 to Lamparter); measurement of the dielectric constant of the strand; mechanical sensing of the strand using coacting rollers (see, for example, U.S. Pat. No. 2,891,287 to Raper); mechanical sensing of the strand using a system for detecting the resonant frequency thereof; measuring optical diffraction of continuous filaments; and, measuring the air flow resistance of the strand in a confined space.

Each of these detection techniques has certain disadvantages which compromise its utility. In the photon absorption technique the shadow of the strand is detected by a photoelectric detector. Such measurements are affected by the shape of the moving strand and the orientation of the fibers with respect to the detector. Dielectric constant methods suffer from erratic long term drifts caused primarily by variations in moisture. The accuracy of mechanical sensing by coacting rollers is limited by the precision of the constituent mechanical parts and cannot be used in high speed applications. Detection of the resonant frequency of a moving fibrous body requires that the body exhibit sufficient elasticity to resonate. Moreover, the detector and detected body should be acoustically isolated from the rest of the textile working system. Optical diffraction methods are limited to continuous filaments where the individual filaments can be separated in a fixed pattern relationship. Finally, air flow resistance measurements suffer from inaccuracies caused by variations in the fiber surface except where continuous filaments are measured.

Accordingly, it is an object of the present invention to provide a method and apparatus for providing a device for controlling a high speed textile working system wherein the control is relatively unaffected by moisture, fiber length, the shape of the worked fibrous body or the orientation of the fibers with respect to a detector.

A known technique for sensing a fibrous strand involves the measurement of the beta particle absorption of the strand. Such a technique is illustrated in U.S. Pat. No. 2,981,986 to Neil. While the beta particle absorption detector has been shown to have good long term stability, the supposed radiation hazard associated with the beta particles has limited the use of the technique.

Accordingly, it is an object of the present invention to provide a method and apparatus for continuously and accurately sensing a traveling fibrous body produced by a textile working system, with accurate short term and long term response, and for controlling the system, without employing sources of radioactivity.

These and other objects and features of the invention will become apparent from the claims and from the following description when read in conjunction with the accompanying drawings.

THE FIGURES

DETAILED DESCRIPTION

Figure 1:
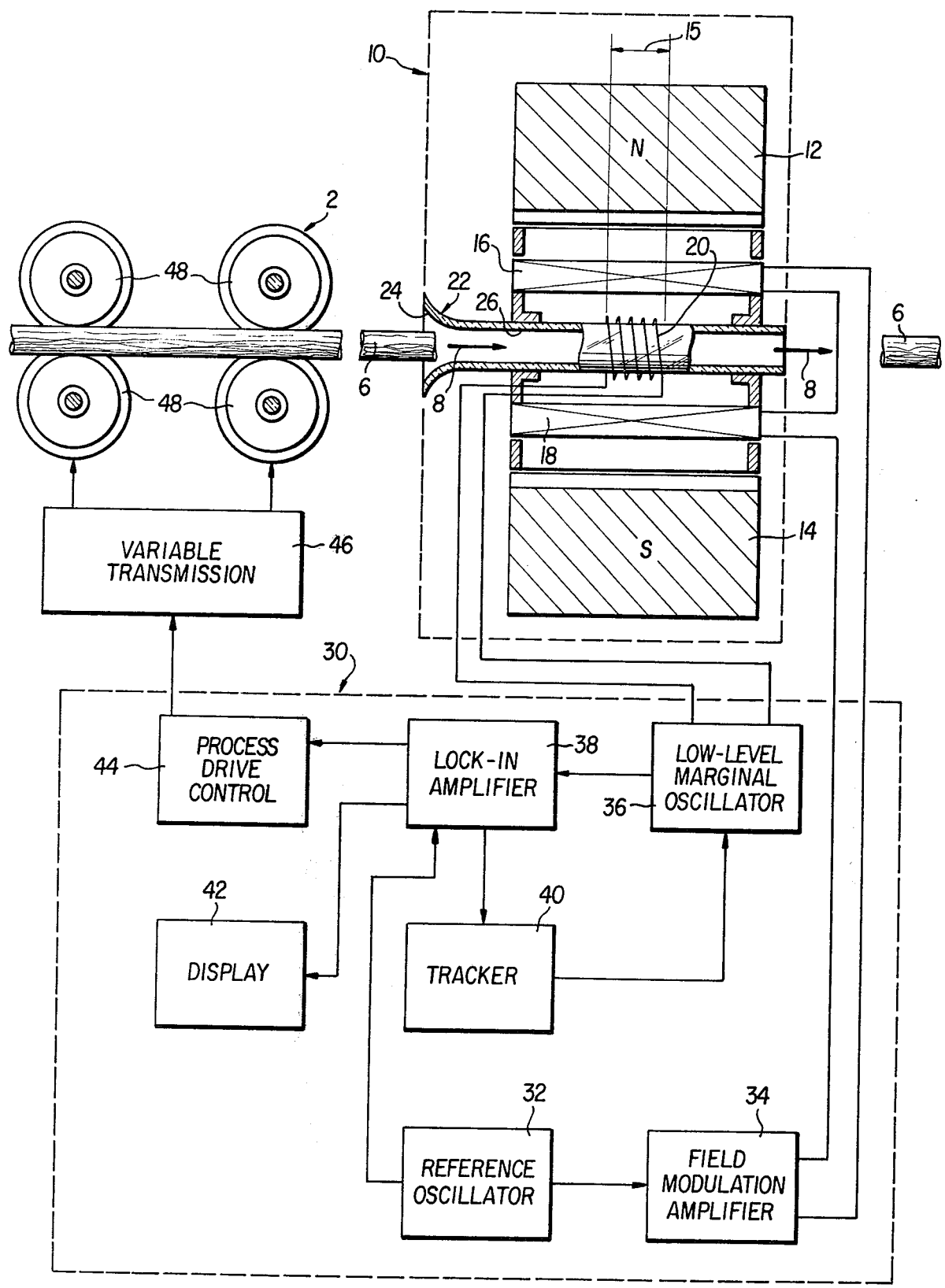
FIG. 1 is a schematic block diagram of a preferred embodiment of the present invention, employed to control a drafting frame.

The present invention is directed to a method and apparatus for controlling a textile working system responsive to a sensed property of the fibrous product of the system. The sensed property is the approximate number of specific types of atoms, such as hydrogen or carbon atoms, in a known length of the fibrous product.

It will be understood that if the fibrous product is pure and homogeneous, the number of specific types of atoms in a known length of the product will have a determinable relationship to the mass of the known length of the product. The numbers of specific types of atoms may be determined by measuring the amount of energy absorbed by the length of fibrous product in nuclear magnetic resonance. Furthermore, it is possible to sufficiently refine such measurements to exclude from detection atoms of the specific type which are not part of the fiber molecules, e.g. hydrogen atoms contained in water carried by the fibrous product.

Certain attributes of the present invention may be recognized by comparison to prior art detection systems described in the background of the disclosure.

Air flow resistance and dielectric constant detectors are affected by surface phenomena of the fibers. For example, the dielectric constant of a body of fibers is affected by moisture which lies on the surface of the fibers. The dielectric constant measurements of such fibers will vary according to the surface area of the fibers and the extent to which the surface is covered with water. Such variations, typically, detract from the usefulness of dielectric measurements for controlling a textile working system.

Detection of the resonance frequency of a fibrous strand is affected by mechanical properties of the strand relating to the way in which the fibers are associated with one another. These mechanical variations, affect, for example, the elasticity of the strand, which, in turn, varies the frequency at which the strand vibrates. Such effects may mask the property of the strand which is sought to be measured: its mass per unit length. Moreover, such resonance frequency detectors should be acoustically isolated from the rest of the textile working system, since typical systems contain a large number of spurious vibration sources. Isolation is far less of a problem where a magnetic resonance is detected.

Likewise in the case of optical detectors, variations in the orientation of the fibers cause variations in the measurements which are made of the fibrous body. In contrast, the detecting and controlling system of the present invention responds to the numbers of specific types of atoms in the fibers within the detector, regardless of the mechanical arrangement of the fibers within the detector.

The measurements made by the present invention involve the detection of the gross external magnetic effects exhibited by atoms of certain elements, such as hydrogen and carbon. This is done by placing a specimen containing the atoms of interest in a constant magnetic field and by measuring the energy required to turn the atomic nuclei end for end.

Certain atomic nuclei may be described as precessing about the direction of the external magnetic field because of the action of the magnetic field.

If an external influence is allowed to act on the system at the same frequency as the frequency of precession, it is possible to change the energy of the system and induce a resonance condition. For this purpose, a small oscillating magnetic field in the radio frequency range may be imposed at right angles to the constant field. If the frequency of the oscillating field is chosen equal to the precession frequency, the nuclei absorb measurable amounts of energy, thereby indicating that resonance is occurring. A rigorous, detailed discussion of the phenomenon of nuclear magnetic resonance is found in a text by Willard, Merritt and Dean entitled, *Instrumental Methods of Analysis,* Chapter 6, page 160 et seq. (D. Van Nostrand Company, Inc., 4th Ed. 1965).

In known nuclear resonance detectors, the spinning nuclei are placed in a constant magnetic field of a known magnitude and the oscillating field is imposed at right angles to the constant field by means of an RF generator connected to a coil in the constant field. The angular frequency of the oscillating field is varied until resonance occurs. At resonance, many spinning nuclei will turn end for end in the field, absorbing energy from the oscillator. This energy absorption can be detected by appropriate electronic techniques.

Heretofore, nuclear magnetic resonance detectors have largely been confined to use in basic research physics to investigate the properties of atomic nuclei and to investigate the constituents of stationary, generally homogeneous test samples. However, nuclear magnetic measurements have been employed in the fluid flowmeter art as illustrated in U.S. Pat. No. 3,419,793 to Genthe et al and U.S. Pat. No. 3,471,774 to Muschinske et al. In these flow meters, sample volumes of a confined flowing fluid are magnetically tagged and the movement of the magnetically tagged volume is monitored by a nuclear magnetic resonance detector to determine volume flow rate. Mass flow may be determined by multiplying the detected volume flow rate by the mass per unit volume of the fluid. However, the mass volume flow rate and mass per unit volume measurements assume a constant reference volume for each sample. This condition is satisfied in the fluid flowmeter art because measurements are made on a generally homogeneous fluid confined in a conduit of known dimensions. These assumptions do not hold true in the case of a moving fibrous body of varying volume, cross section and mass per unit length.

The use of principles of nuclear magnetic resonance in a preferred embodiment of the present invention for the controlling of a textile working system requires the recognition of a number of additional facts.

Both hydrogen and carbon nuclei are susceptible to nuclear magnetic resonance and both are present in substantial quantities in both natural and man made fibers. The range of the ratio of hydrogen atoms to total molecular weight ranges from a high of 0.10 for nylon 6 to 0.062 for cotton and 0.059 for acrylics. However, the number of hydrogen atoms per unit mass of a particular kind of fiber is substantially constant.

The amount of energy absorbed from a nuclear magnetic resonance detector by a sample is proportional to the number of resonating nuclei in the sample. Thus, where the sample is a fibrous strand and the detector is operated at the resonance of the hydrogen nuclei, it has been found that a signal proportional to the absorbed energy is related in value to the mass of the absorbing fibrous material. Where water is present with the fibers and it is desired to eliminate the effects caused by the water, a detector of sufficient resolution may be used to permit the so called "water line" to be filtered out of the nuclear magnetic resonance spectrum.

In the present invention, a traveling fibrous strand is funnelled through a nonmagnetic trumpet through a nuclear magnetic resonance detector sense coil. The detector may provide a virtually instantaneous "snap shot" of the mass of a known length of the traveling fibrous strand in the detector. The known length corresponds approximately to the length of the RF coil of the nuclear magnetic resonance detector. Alternatively, where such a detection is not available, analysis of the analog derivative of the signal from the detector caused by all hydrogen atoms in the fibers and the water may permit the effects of the water to be eliminated.

More specifically, a detector may be provided for producing a signal related in value to the variations in the mass per unit length of a traveling fibrous strand such as a drafted sliver from a drafting frame. The detector may include a permanent magnet for imposing a magnetic field on the traveling fibrous strand and a coil for inducing nuclear magnetic resonance in a known length of the traveling fibrous strand within the field. A signal is produced related in value to the radio frequency electrical energy absorbed from the coil by the traveling fibrous strand at resonance. The detector may be used for controlling a textile working system such as a drafting frame. Where the detector is used in conjunction with a drafting frame, the output signal produced by the detector may be used for varying the draft imparted to the sliver.

The strand, whose linear mass characteristics are to be determined, is passed through a sensing coil which is positioned in a strong magnetic field, substantially uniform along a length of the strand. A field modulation coil may be provided for periodically varying the field strength of the strong magnetic field by a small percentage. A sensing coil is oriented so that its axis is perpendicular to the strong magnetic field, and forms the tank circuit of a marginal oscillator which drives the sensing coil. The oscillator is initially tuned to the hydrogen nuclei resonance frequency and the tracking characteristics of the circuit force the system to remain tuned to the resonance as long as the fibrous strand is located within the coil. The oscillator may be fine tuned to avoid the resonance frequency of hydrogen nuclei in any water molecules which may be present.

The marginal oscillator produces an output signal related in value to the number of absorbing hydrogen nuclei within the sensing coil. This signal can be used to drive a mass per unit length indicator and to control a servo mechanism in the textile working system.

FIGURE 1

The Detector Station

Referring now to FIG. 1, a fiber drafting frame 2 is shown with a nuclear magnetic resonance detector and controller for controlling the drafting frame responsive to variations detected in the mass per unit length of the sliver 6 taken from the drafting frame. As indicated by the arrows 8, the traveling sliver 6 enters a detector station 10 and passes through the detector station to exit the station, whereupon the sliver may be further processed.

The detector station 10 includes a magnet for providing a substantially uniform magnetic field generally perpendicular to the direction of travel of a portion of the sliver 6 in the detector station. In the Figure a north pole piece 12 and a south pole piece 14 of such a magnet are shown oriented to provide a strong magnetic field which is vertical in the place of the Figure and which is of substantially uniform strength along a length of the sliver indicated by the double headed arrow 15. The strong uniform magnetic field may, advantageously, be provided by a 3 to 5 kilo Gauss permanent magnet with a ¾" gap. It will be readily understood however, that an electromagnetic producing a magnetic field of equivalent or greater strength and uniformity, may be substituted for the permanent magnet.

The field created by the pole pieces 12 and 14 may be periodically varied by means of sweep coils 16 and 18. The field modulation induced by the sweep coils may be on the order of a few Gauss, the field strength varying periodically at an audio frequency, such as 440 Hertz.

Near the center of the pole pieces, where the magnetic field produced therethrough is substantially uniform, a perturbing field coil 20 may be located. Advantageously, the perturbing field coil is disposed in surrounding relationship with respect to the length 15 of the traveling sliver 6 within the sensor. The perturbing field coil imposes a relatively weak, periodically varying magnetic field perpendicular to the strong magnetic field. The frequency of periodic variation of the perturbing magnetic field is chosen so that nuclear magnetic resonance may be induced in selected hydrogen nuclei in the length 15 of the traveling sliver at the field strength of the strong magnetic field. This frequency is a radio frequency on the order of 5-10 mega Hertz and depends on the strength of the magnetic field.

A portion of the sliver 6 traveling through the sensor may be contained by a nonmagnetic trumpet 22 having a mouth portion 24 for receiving the sliver and a narrowed portion 26 of relatively smaller internal diameter than the mouth around which the perturbing coil may be wrapped. Advantageously, the trumpet 22 may be made of glass or ceramic. The perturbing coil surrounds the length of the strand indicated by the double-headed arrow 15.

The Detection and Control Circuitry

The detection and control circuitry 30, shown in FIG. 1, provides a periodically varying signal to the sweep coils 16 and 18, and to the reference input of the lock-in amplifier. The amount of energy absorbed from the perturbing field coil 20 by the sliver at resonance is detected and may provide an indication of the mass of a unit length of the sliver surrounded by the perturbing field coil. The drafting frame 2 is controlled by the detector and controller circuitry responsive to variations in the amount of energy absorbed by the sliver at resonance.

The detection and control circuitry 30 includes a reference oscillator 32 for providing a periodically varying, audio frequency signal to a field modulation amplifier 34 which, in turn, is employed to drive the sweep coils 16 and 18. A low level marginal oscillator 36 provides a low amplitude radio frequency signal to the perturbing field coil 20 at the resonance frequency of the hydrogen nuclei.

It is possible to excite a large portion of the hydrogen atoms within the length 15 of the sliver 6 if enough energy is introduced into the sliver by the perturbing field coil. This effect is described as "saturation", and, when it occurs, the amount of energy absorbed by the sliver may bear a non-linear relationship to the total number of hydrogen atoms in the length 15 of the sliver. Accordingly, the low level marginal oscillator produces a controlled, low level signal, typically on the order of a few milliwatts, to avoid saturating the nuclei of the fibrous body within the surrounding coil. A low level marginal oscillator of a type known in the prior art is disclosed in Vol. 43, No. 8 of the publication *Review of Scientific Instruments,* beginning at page 1129.

The low level marginal oscillator 36 provides a signal related in value to the energy absorbed by the hydrogen nuclei in the length 15 of the sliver 6 within the surrounding coil. This signal is applied to a lock-in amplifier 38. The lock-in amplifier also receives the audio frequency signal provided by the reference oscillator 32. The lock-in amplifier 38 performs phase coherent detection of small fluctuations in the signal from the low level marginal oscillator induced by variations in the numbers of hydrogen atoms in the length of the traveling sliver. Stated another way, the lock-in amplifier facilitates detection of the signal related in value to energy absorption by the fibrous body in a fixed phase relationship with respect to the signal being imposed on the sweep coils 16 and 18. It will be understood that, if the low level marginal oscillator provides a signal to the surrounding coil at a fixed frequency, resonance will be induced in the hydrogen nuclei only when the strong magnetic field is swept through a particular field strength which satisfies the resonance condition. The absorption signal produced by the marginal oscillator thus varies in synchrony with the reference oscillator and can be phase coherently detected with respect to it by the lock-in amplifier 38.

A tracker circuit 40 receives an output signal from the lock-in amplifier 38 and provides a control signal to the low level marginal oscillator 36. This control signal is employed to tune the low level marginal oscillator to a resonance frequency of the hydrogen nuclei. Thus the tracker circuit 40 facilitates the elimination of errors due to fluctuations in operating conditions, e.g., variations in the strong magnetic field, sliver temperature, resonance frequency of hydrogen in the fibers, etc. A tracker circuit known in the prior art is illustrated in the above referenced article in the *Review of Scientific Instruments*.

The lock-in amplifier 38 produces a signal related in value to the number of hydrogen atoms per unit length of the traveling sliver surrounded by the perturbing field coil 20. This signal may be supplied to a display apparatus 42, for example, a digital LED display. The display apparatus may provide a nearly instantaneous readout of the mass per unit length of the traveling fibrous strand produced by the drafting frame 2.

The output signal of the lock-in amplifier 38, may also be applied to a process drive control circuit 44. The process drive control circuit, in turn, may provide a control signal to the textile working system. As shown in the Figure, the control signal provided by the process drive control circuit 44 is applied to a variable transmission 46 for the drafting frame 2. The variable transmission may be operative to change the drafting ratio of the drafting frame 2, by changing the rotation rates of rollers 48 with respect to one another in order to continuously compensate for detected variations in the sliver.

Operation

In operation, the sliver produced by the drafting frame system is passed through the trumpet 22 of the detector station. The sliver is impinged by a strong, substantially uniform magnetic field which has a low level ripple field superimposed on it by the sweep field coils 16 and 18. The length 15 of the sliver within the sensor head is also impinged by a varying magnetic field provided by the perturbing field coil 20. The frequency of this second field may be tuned by the tracker 40 to have a frequency characteristic of a hydrogen resonance of the sliver. Energy from the perturbing coil 20 is absorbed by the length 15 of the sliver at resonance, in an amount depending on the numbers of hydrogen atoms in the length of the fibrous strand within the perturbing coil 20. The marginal oscillator responds to this absorption by adjusting its operating conditions in such a way as to keep the amplitude of the oscillator signal at a constant value. This shift of operating point is detected to provide a signal related in value to the numbers of hydrogen atoms in a unit length of the sliver.

The above-described system could be operated in a static mode, i.e. without employing the sweep field coil 16 and 18, if there were no drift producing influences and no system noise, and if there were no tendency for the low level marginal oscillator 36 to saturate the hydrogen nuclei in the sliver. However, since these effects are normally present, the sweep coils are provided to sweep periodically through the value at which the hydrogen resonance frequency coincides with the marginal oscillator frequency. The absorption signal produced by the marginal oscillator thus varies in synchrony with the reference oscillator and can be phase sensitively detected with respect to it by the lockin amplifier. The signal to noise ratio is thereby greatly enhanced. The use of the sweep coils to provide a slowly varying ripple on the strong magnetic field also reduces the possibility that the length 15 of the fibrous strand within the perturbing coils will be saturated, since that length of material is in resonance for only a part of each sweep period.

FIGURE 2

Figure 2:
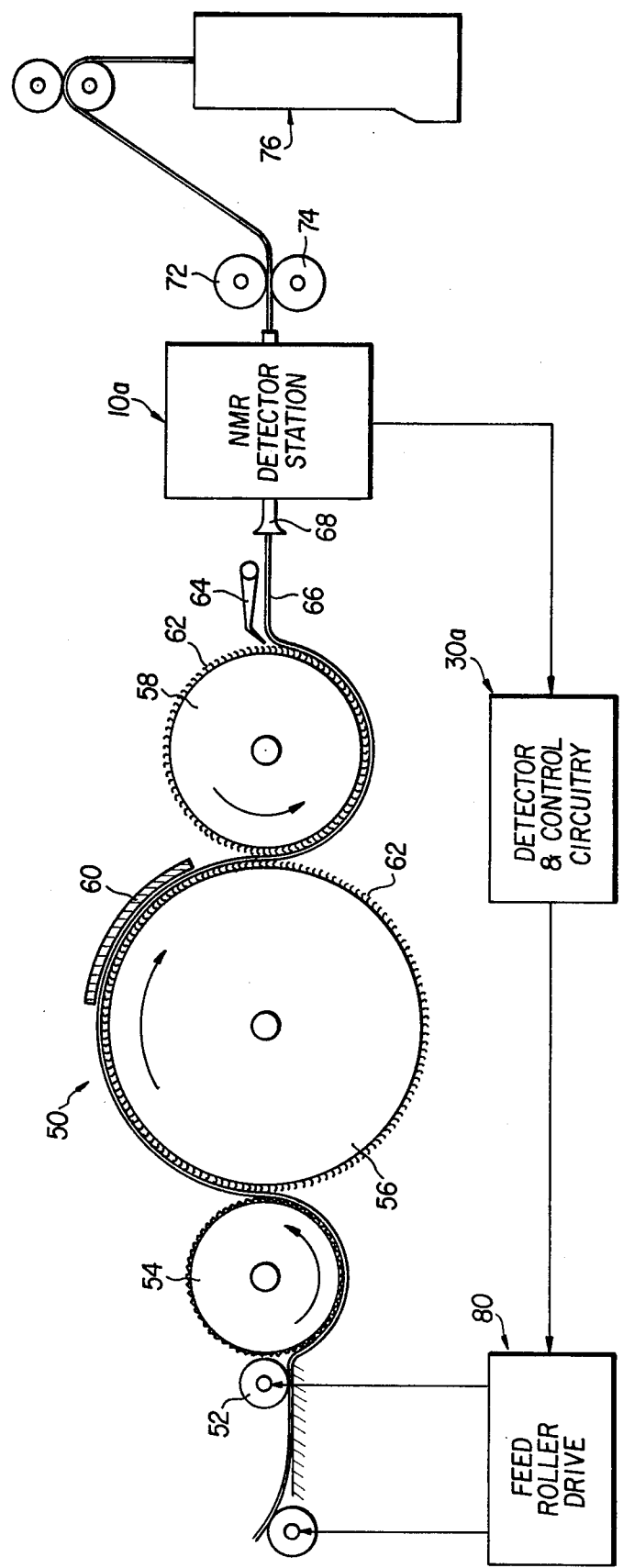
FIG. 2 is a schematic diagram of a carding machine employing the controlling system of the present invention.

Referring now to FIG. 2, a carding machine 50 is shown, which is controlled by a nuclear magnetic resonance detector and controller such as described in connection with FIG. 1. It will be understood, however, that the detector and controller of FIG. 1 may be employed to control any apparatus in a textile working system which is capable of producing variations in the mass per unit length of the fibrous product.

The carding machine shown in FIG. 2 is of conventional design. A feed roller 52 and licker cylinder 54 provide a fibrous fleece to a card cylinder 56. The card cylinder 56 rotates in the direction indicated by the arrow so as to carry the fleece downwardly toward a doffer cylinder 58. The card cylinder 56 and the doffer cylinder 58 each have a cylindrical shell covered with a card clothing 62 formed of hooked wires. The fleece is received by the doffer cylinder 58 having first been acted on by the overhead flat 60 in the conventional manner.

The surface speed of the card cylinder 56 and the direction of rotation of the cylinders is such that the fleece is carried downwardly by the rotation of the card cylinder 56 into contact with the slower rotating card clothing of the doffer cylinder 58. This serves to condense the fleece and to transfer the fleece from the carding cylinder to the doffer cylinder. The fleece is then carried downwardly by the doffer cylinder 58 where it may be removed by a vibrating doffer comb 64.

As the fibrous body 66 leaves the surface of the doffer cylinder 58 it may be passed through a sensor trumpet 68 of a nuclear magnetic resonance detector station 10a such as was described in connection with FIG. 1. After the strand exits the trumpet, it may be drawn by calendar rolls 72 and 74 and passed to a coiling mechanism and can 76.

The nuclear magnetic resonance detector station and detector and control circuitry 30a may be employed to provide a control signal to a feed roller drive 80 for controlling the fibers fed to the carding machine responsive to variations in the fibrous body 66 produced by the carding machine, which passes through the nuclear magnetic resonance detector station 10a in a manner similar to that described in connection with the detector station 10 of FIG. 1. In this manner, continuous control may be provided for the carding machine to prevent short term and long term variations in the fibrous body produced thereby.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made without departing from the spirit of the invention.

What is claimed is:

1. An apparatus for controlling a fiber drafting system, comprising:
   detector means for producing a signal related in value to variations in the mass per unit length of the fibrous material in a unit length of the drafted sliver including:
   means for providing a magnetic field impinging on the drafted sliver; and,
   means for inducing nuclear magnetic resonance in a predetermined length of the drafted sliver within the field and for producing a signal related in value to the energy absorbed by the length of the sliver at resonance; and,
   means for varying the draft imparted to the sliver responsive to variations in the signal produced by the detector means, to vary the mass of fibrous material per unit length of the sliver.

2. A method of controlling a textile working system comprising the steps of:
   producing a signal related in value to the number of a specific type of atom bonded to fibrous material in a known length of a traveling fibrous body being worked in the system by detecting the amount of energy absorbed by the length of the fibrous body at nuclear magnetic resonance; and
   varying an operating parameter of the textile working system responsive to variations in said signal to vary the fibrous mass per unit length.

3. In a textile working system producing a traveling elongated fibrous body having a fibrous mass per unit length, an improvement for controlling said mass per unit length comprising the steps of:
   disposing a portion of the traveling elongated fibrous body in magnetic field;
   inducing nuclear magnetic resonance in the hydrogen nuclei in a length of the fibrous body within the field;
   producing a signal related in value to the energy absorbed by the length of the fibrous body at resonance; and,
   varying an operating parameter of the textile working system responsive to the signal related in value to the energy absorbed by the length of the fibrous body to vary the fibrous mass per unit length of the fibrous body.

4. An apparatus for detecting variations in the mass per unit length of a traveling fibrous strand, comprising:
   means for providing a substantially uniform magnetic field generally perpendicular to the direction of travel of a portion of the fibrous strand;
   sweep coil means for providing a first periodically varying magnetic field generally parallel to the uniform magnetic field;
   means, including a coil disposed in surrounding relationship to a predetermined length of the portion of the fibrous strand, for providing a second, periodically varying magnetic field perpendicular to the substantially uniform magnetic field to induce nuclear magnetic resonance in the length of the fibrous strand said means also including an oscillator for providing a generally constant amplitude signal to the surrounding coil at the resonance frequency of hydrogen nuclei bound in the length of the fibrous strand; and,
   means for producing a signal related in value to the energy absorbed from the surrounding coil by the length of the fibrous strand at resonance.

5. The apparatus of claim 4 further comprising means for suppressing detection of energy absorption caused by hydrogen bonded in water carried by the fibrous strand.

6. The apparatus of claim 4 wherein the constant amplitude is selected to inhibit saturation of the hydrogen nuclei at resonance.

7. The apparatus of claim 4 wherein the signal related in value to the energy absorbed from the surrounding coil is phase coherently detected with respect to the first periodically varying magnetic field.

8. The apparatus of claim 4 further comprising non-magnetic means for containing the traveling fibrous strand as it moves through the surrounding coil.

9. The apparatus of claim 8 wherein the containing means comprises a non-magnetic glass or ceramic tube with a mouth portion for receiving the traveling fibrous strand and a body portion, with a relatively smaller internal diameter than the mouth portion, around which the surrounding coil is wrapped.

10. An apparatus for controlling a textile working system, comprising:
    means for producing a signal related in value to the number of a specific type of atom in a known length of a traveling fibrous body being worked in the system by detecting the amount of energy absorbed by the length of the fibrous body at nuclear magnetic resonance; and
    means for varying an operating parameter of the textile working system responsive to variations in said signal.

* * * * *